United States Patent
Barclay et al.

[11] Patent Number: 5,972,711
[45] Date of Patent: *Oct. 26, 1999

[54] MICROWAVE ASSISTED CHEMICAL PROCESSES

[75] Inventors: David A. Barclay, Charlotte; William Edward Jennings, Wingate; Edward E. King, Charlotte, all of N.C.

[73] Assignee: CEM Corporation, Matthews, N.C.

[ * ] Notice: This patent is subject to a terminal disclaimer.

[21] Appl. No.: 09/121,007

[22] Filed: Jul. 22, 1998

Related U.S. Application Data

[63] Continuation of application No. 08/924,628, Sep. 5, 1997, Pat. No. 5,840,583, which is a continuation of application No. 08/538,603, Oct. 3, 1995, abandoned.

[51] Int. Cl.⁶ .......................... G01N 33/00; G01N 35/08; G01N 33/20; G01N 1/00
[52] U.S. Cl. ................................. 436/55; 436/62; 436/73; 436/74; 436/79; 436/80; 436/81; 436/82; 436/83; 436/84; 436/103; 436/106; 436/114; 436/115; 436/155; 436/157; 436/174; 436/175; 436/182; 422/78
[58] Field of Search ............................ 436/55, 62, 106, 436/73–84, 103, 114–115, 155, 157, 174–175, 182; 422/78

[56] References Cited

U.S. PATENT DOCUMENTS

| | | |
|---|---|---|
| 4,444,723 | 4/1984 | Matsumaru et al. . |
| 4,681,740 | 7/1987 | Commarmot et al. .................... 422/78 |
| 5,205,050 | 4/1993 | Masaaki et al. . |
| 5,840,583 | 11/1998 | Barclay et al. ........................... 436/55 |

FOREIGN PATENT DOCUMENTS 63-236766  10/1988  Japan .

OTHER PUBLICATIONS

J. Berlan et al. *Tetrahedron Lett.* 1991, 32, 2363–2366.
E.–U. Schlünder *Trans. I. Chem. E.* 1993, 71A, 622–628.
E. Florence et al, *Analyst* 1979, 104, 378–381.
D.W. Mincey et al. *Analytica Chimica Acta* 1992, 264, 97–100.
M.H. Feinberg et al. *Analytica Chimica Acta* 1993, 272, 83–90.
H.A. McKenzie *Trends in Analytical Chemistry* 1994, 13, 138–144.

*Primary Examiner*—Arlen Soderquist
*Attorney, Agent, or Firm*—Philip Summa

[57] ABSTRACT

A method for microwave assisted chemical processes is disclosed that comprises applying sufficient microwave radiation to a temperature-monitored mixture of reagents, with at least one of the reagents being thermally responsive to electromagnetic radiation in the microwave range, and based on the monitored temperature, to maintain the added reagents at or closely about a predetermined temperature while substantially avoiding thermal dilution (or before substantial thermal dilution can occur) that otherwise would have been caused by the addition of the reagents to one another.

40 Claims, 2 Drawing Sheets

MICROWAVE ASSISTED CHEMICAL PROCESSES

This application is a continuation of Ser. No. 08/924,628, filed Sep. 5, 1997, now U.S. Pat. No. 5,840,583, which is a continuation of Ser. No. 08/538,603, filed Oct. 3, 1995, now abandoned.

FIELD OF THE INVENTION

The present invention relates to microwave processing of laboratory-type samples, and for carrying out associated microwave assisted chemical reactions. This application is related to U.S. Pat. No. 5,840,583 to Barclay et al. for, "Microwave Apparatus for Controlling Power Levels in Individual Multiple Cells," and which is incorporated entirely herein by reference.

BACKGROUND OF THE INVENTION

"Microwave" is the term generally used to describe the portion of the electromagnetic spectrum that has wavelengths ($\lambda$) between the far infrared and the radio frequency; i.e. between about one millimeter and about 30 centimeters, with corresponding frequencies ($v$) in the range from about 1 to 100 gigahertz (GHz). Microwave radiation has a number of useful purposes, including spectroscopy, communication, navigation, and medicine, but one of the most common uses is as a heating technique, particularly for food; i.e. the almost ubiquitous "microwave oven."

Because heating is such an integral step in so many chemical processes, the potential for using microwave as a heating source for chemical processes has been recognized for some time, and a number of devices and methods have been developed for microwave assisted chemistry, including analytical chemistry. Analytical chemistry can be roughly defined as those methods used to identify one or more of the components (compounds, elements and mixtures) in a sample of material, as well as the determination of the relative quantity of each component in such a sample. As is well known to those of ordinary skill in the chemical arts, analytical chemistry is a major area or interest from a practical standpoint.

The process of identifying she components is generally referred to as "qualitative" analysis, and the determination of the amounts of various components is generally referred to as "quantitative" analysis. Examples of qualitative and quantitative analyses are numerous. Specific ones include (but are certainly not limited to) measurement of pollutants or other components of gases; identification of components in blood or other tissue for medical purposes; the production, control, and safety of food products; the manufacture of major industrial materials such as acids, organic chemicals, steel and the like; and the analysis of soil and other related materials for agricultural and related purposes. Additionally, such quantitative and qualitative analyses is often foundational to fundamental research activity in the basic sciences such as chemistry, biology, and biochemistry.

In many cases, quantitative and qualitative analyses are proceeded by preliminary steps that are required to give the analytical data the appropriate accuracy and significance. Typical steps include gathering an appropriate sample of the material to be analyzed, turning that into an appropriate mixture or composition for analytical purposes, and often drying the sample or otherwise determining its moisture content. For example, "oven drying" is a classical method for drying a sample (and thus determining its moisture content) based on the change in weight during drying. As is known to those familiar with chemical processes, oven drying is generally time consuming and in many cases must be followed by an appropriate cooling period, because a hot sample (or even a warm one) can cause problems during the weighing process. For example, a hot sample tends to set up convection air currents that disturb an otherwise sensitive balance.

Analytical chemistry also often requires performing measurements on solutions rather than on raw materials. Thus, the particular composition to be identified or measured (the "analyte") must often be converted into a soluble form. Such treatment usually requires powerful reagents such as concentrated mineral acids and strenuous treatment including relatively high temperatures. Microwave radiation can be used to heat such solutions, particularly when they are aqueous or aqueous based (e.g. mineral acids, such as hydrochloric, nitric and sulfuric), but offers the disadvantages noted above.

Similarly, analysis of an elemental composition or organic sample generally requires a relatively severe treatment to convert compounds into elemental forms that are either convenient or even necessary in many common analytical techniques. Such treatments usually represent oxidation of the sample and thus include conversion of carbon to carbon dioxide and hydrogen to water or water vapor. Some of the oxidation procedures that use liquid oxidizing agents such as the mineral acids are referred to as "wet ashing," "wet-oxidation," or "digestion."

As alternative, dry ashing or dry oxidation usually refers to the processes in which the organic compound is ignited in air or oxygen. In each case, the requirement for high temperatures makes microwave processes attractive apart from the noted disadvantages.

As an another chemical analysis technique where heat can be useful, many compounds are separated by the use of extraction procedures; i.e. taking advantage of the distribution of a solute between two immissible phases. Because extraction is fundamentally an equilibrium process, the application of heat can be particularly useful, and indeed the use of microwaves for this purpose has been suggested by Paré et al. in processes described in U.S. Pat. No. 5,002,784 among others.

Other uses of heat in chemical processes include simple evaporation of liquids for the straightforward purpose of decreasing the volume of a solution without loss of a nonvolatile solute. As noted above, drying or igniting a sample to constant weight also requires heat, and thus microwave processes form an attractive alternative to the classical use of burners, hot plates, and convection ovens.

For several generations of chemists, heating has typically been done with the classic bunsen burner, or more recently heated plates ("hot plates"). Nevertheless, the use of microwave energy is entirely appropriate, if all other factors are likewise conducive to use of the microwaves. Because water and a number of organic compounds are good absorbers of microwave energy, the use of microwaves provides an attractive alternative, at least in concept, to such traditional heating methods.

Accordingly, there are a number of commercially available microwave devices that are designed for laboratory use.

When microwave devices are used for chemical reactions, a common technique for maximizing their efficiency is to run a plurality of reactions in separate containers ("vessels") at the same time in a single, relatively large resonator. The containers are typically made of a microwave transparent material such as an appropriate plastic or ceramic. Generally a plurality of two or more containers, and sometimes as many as fifty, are placed in the cavity of a laboratory microwave oven and then radiated with the microwaves. In a typical circumstance, one of the vessels is monitored for pressure, temperature, color change, or some other parameter that measures or indicates the progress of the reaction in that single vessel. The remaining unmonitored vessels are considered to have behaved identically to the monitored vessel. This is, however, only a best estimate, as is recognized by those of ordinary skill in this art. Accordingly, the methods carried out by such typical apparatus offer less-than ideal results in many circumstances.

Processes for heating chemical reactions also have other limitations, however, a number of which arise from the volatility of many compounds, particularly organic compounds, at higher temperatures. As well known to chemists, water's boiling point of 100° C. is relatively high for such a small molecule and results from its propensity for hydrogen-bonding. Many larger organic molecules have lower boiling points, meaning that they become volatile at lower temperatures. Because gas volumes expand rapidly with temperature (pV=nRT), analytical reactions that produce gases must be either carefully vented or carried out in pressure-resistant or pressure-controlled equipment.

Alternatively, if a particular analysis requires heating an otherwise volatile material beyond its atmospheric boiling point while preventing its evaporation, the reaction must be carried out at elevated pressures, and will accordingly require pressure vessels and associated operating parameters and safety equipment.

For example, analysis reactions such as digestion in which the oxidizing agent is concentrated (70%) nitric acid ($HNO_3$; boiling point 120.5° C.) must either be limited to temperatures below 120.5° C. at atmospheric pressure, or must be carried out at elevated pressures in order for the temperature to be raised above 120.5° C.

Accordingly, the need exists for a technique for heating and driving chemical reactions that can be carried out at elevated temperatures and atmospheric pressure, and that can accordingly incorporate reagents that would otherwise require gas and pressure control under most circumstances.

OBJECT AND SUMMARY OF THE INVENTION

Therefore, it is an object of the present invention to provide a method of increasing the rate of chemical reactions while controlling an elevated temperature for the reactions. The invention meets this object with a method that comprises applying sufficient microwave radiation to a temperature-monitored mixture of two reagents, with at least one of the reagents being-thermally responsive to electromagnetic radiation in the microwave range, and based on the monitored temperature, to maintain the added reagents at or closely about a predetermined temperature while substantially avoiding thermal dilution (or before substantial thermal dilution can occur) that otherwise would have been caused by the addition of the reagents to one another.

DETAILED DESCRIPTION

Figure 1:
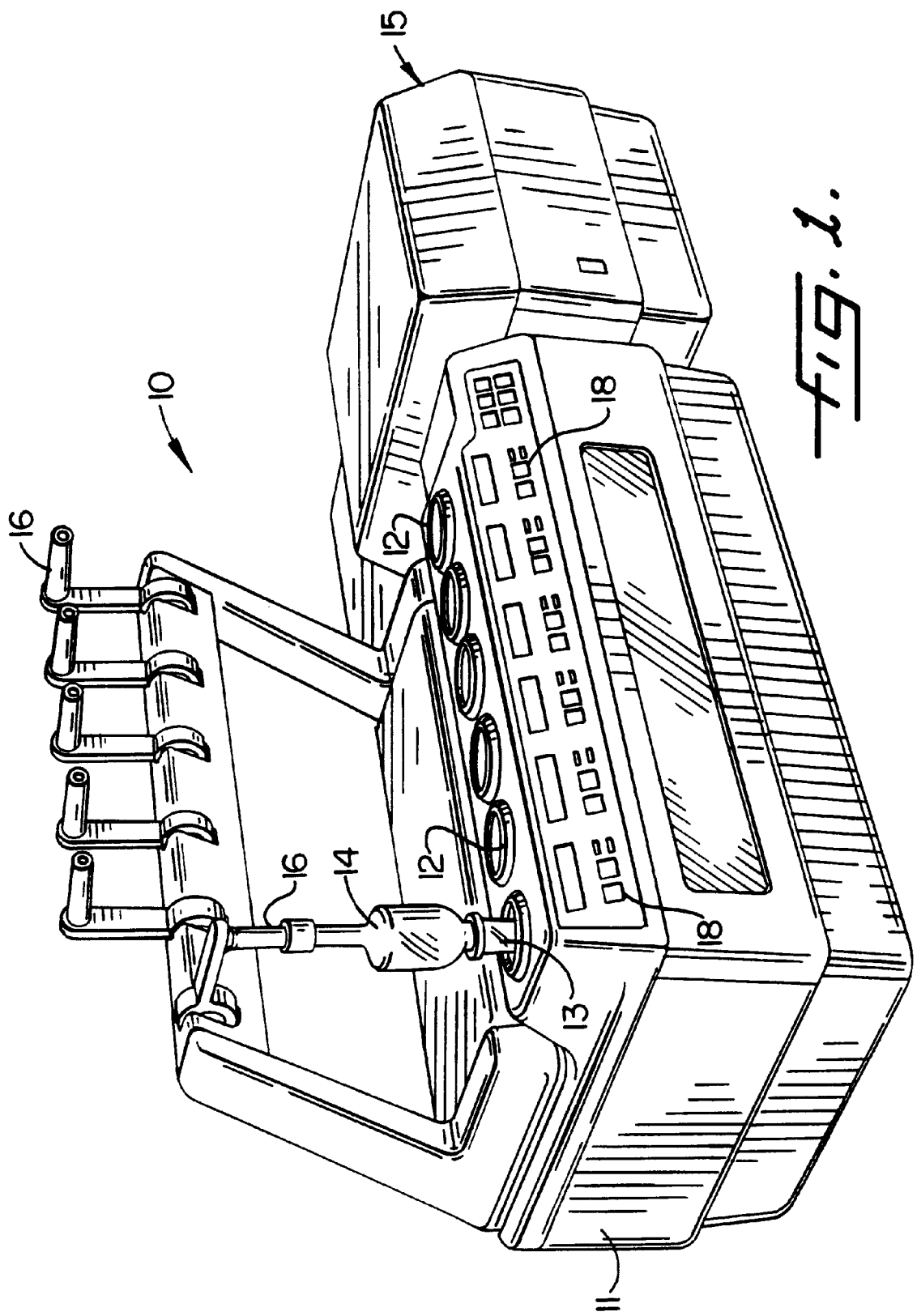
FIG. 1 is a perspective view of an apparatus used to carry out the method of the present invention.

The invention is a method of increasing the rate of chemical reactions while controlling an elevated temperature for the reactions. In a first aspect, the method comprises adding a portion of a second reagent to a heated portion of a first reagent with at least one of the reagents being thermally responsive to electromagnetic radiation in the microwave range. The temperature of the added first and second reagents is monitored as the second reagent is added, and sufficient microwave radiation is applied to the added first and second reagents based on the monitored temperature to maintain the added reagents at or closely about the predetermined temperature while substantially avoiding thermal dilution (i.e. before substantial thermal dilution— i.e. the cooling effect that a cooler reagent has when added to a warmer reagent—can occur) that would otherwise be caused by the addition of the reagents to one another.

In preferred embodiments, the step of applying sufficient microwave radiation can further comprise moderating the microwave radiation by moderating the passage of microwaves from a microwave source to the reagents without moderating the production of microwaves by the source; i.e., the production of microwaves from the source remains constant, but the amount of energy reaching the reagents is proactively moderated. Stated alternatively, the step of applying microwave radiation comprises applying the microwave radiation on a time-continuous basis while moderating the amount of the continuously applied energy that is permitted to reach the added first and second reagents or to reagents in a solvent system as described later herein. In this regard, the apparatus described in the copending incorporated application is particularly suitable.

In a particular embodiment, the step of adding the second reagent to the first reagent comprises adding the second reagent to a proportionally larger portion of the first reagent. Furthermore, the method is useful with both liquids and solids, so that the steps of adding the second reagent to the first reagent can comprise adding a liquid to a liquid, a solid to a solid, a liquid to a solid, or a solid to a liquid. Under other circumstances, a gas could comprise one of the added reagents.

One of the advantages of the invention is that the steps of adding the reagents, monitoring the temperature, and applying microwave radiation can all be carried out with the reagents at atmospheric pressure, thus avoiding the problems otherwise associated with high temperature chemical reactions.

Accordingly, in embodiments where a liquid is added to a liquid, one useful application includes maintaining the first liquid at atmospheric pressure and at a predetermined temperature that is above the boiling point of the second reagent that is added. In this way, the first reagent liquid provides a thermal environment for the second reagent liquid that is well above the boiling point of the second liquid, and thus produce temperatures for reaction purposes that are otherwise higher than those at which the second liquid could be used, particularly at atmospheric pressure. Because the temperature is monitored, and microwave radiation applied, the thermal dilution that would otherwise result from the addition of the usually cooler second reagent can be minimized or eliminated.

In specific examples, the various boiling points of the common mineral acids can be used to make the choice. For example, the boiling points of several common mineral acids are as follows (some references differ slightly):

| Acid | Boiling Point |
|---|---|
| HCl | 110° C. |
| $HNO_3$ | 120.5° C. |
| $H_2SO_4$ | 330° C. |

This data demonstrates that using the method of the invention, sulfuric acid can be used as the first reagent and heated to a temperature well above the boiling point of nitric acid, but without itself boiling. When nitric acid is then added for reactive purposes, it reacts at temperatures well above those at which it could ordinarily react at atmospheric pressure. It will be understood of course that carrying out the reaction at temperatures above the boiling point of one of the reagents is advantageous, but not required, and that the use of a higher than ordinarily available temperature is the useful feature. As noted above, this is most conveniently carried out when a small portion of a second reagent is added to a proportionally larger portion of the first reagent.

The method can further comprise the step of heating the first reagent prior to the step of adding the second reagent, and the step of applying microwave radiation can comprise applying the microwave radiation on a time-continuous basis while moderating the amount of the continuously applied energy that is specifically applied to the added reagents.

In a preferred embodiment, the step of monitoring the temperature of either of the reagents or their admixture comprises monitoring the infrared radiation emitted from the reagents using a common device such as an infrared pyrometer. As described in U.S. Pat. No. 5,840,583 to Barclay et al., the pyrometer can be operatively associated with a control system that moderates the passage of microwave energy to the reagents based upon the temperature monitored by the pyrometer.

It will be understood of course that an infrared pyrometer is exemplary rather than limiting of the present invention, and that other technique and tools for temperature measurement could be used.

Because the pyrometer continuously measures the temperature, and because microwave radiation acts quickly—indeed almost instantaneously—upon a sample, the step of applying microwave radiation can comprise applying sufficient radiation to heat the sample to, and keep the sample at a predetermined temperature, or within a predetermined temperature range, it being understood that for some purposes a very specific temperature is required, while for other purposes, operating within a defined range will provide the appropriate results.

In another embodiment, the invention can comprise adding respective portions of a first reagent and a second reagent to a heated and proportionally larger portion of a solvent system that is responsive to microwave radiation, and with the solvent system also at atmospheric pressure and at a predetermined temperature. Stated differently, the solvent system can be active or inert with respect to the reaction to be carried out, but in either case can provide the thermal response to microwave radiation that is helpful in first heating the solvent system and then derivatively heating the first and second reagents based on their thermal contact with the microwave heated solvent system. As in the other embodiments, where a heated solvent system is used, liquid or solid reagents can be added while the solvent system is maintained at a predetermined temperature that is above the boiling point of at least one of the first or second reagents, or potentially both.

It will be well understood by those familiar with chemical analysis, that the invention will be particularly useful with methods such as extraction, oxidation reactions, digestion, dry ashing, wet ashing, or indeed any reaction in which control of temperature or addition of heat can have a favorable or otherwise useful effect on the reaction system for the particular purposes for which the reaction is being carried out.

In another embodiment, the invention can comprise the steps of adding an incremental portion of a second reagent to a heated and proportionally larger portion of a first reagent, with at least one of the reagents being thermally responsive to electromagnetic radiation in the microwave range, preferably the first reagent. The temperatures of the first and second reagents are monitored as the second reagent is added, and the exhaustion of the incrementally added second reagent is identified based upon the change in the monitored temperature. Thereafter, another Incremental portion of a reagent is added to the heated and proportionally portion of the first reagent. The second incremental portion added can be the same as the first reagent, or can be a different reagent.

Additionally, adding one of the reagents on a drop-by-drop basis also helps prevent thermal dilution of the overall process.

In yet another embodiment, the invention can comprise the method of controllably heating a sample to dryness without unintentionally carrying the drying process beyond a desired degree. In this embodiment, the method comprises heating a moisture-containing sample which is responsive to microwave radiation with microwave radiation while continuously monitoring the temperature of the sample, and then immediately stopping the microwave heating once the change in temperature indicates that all of the moisture in the sample has been removed by the microwave heating.

It will be understood, of course, that although the term "moisture" often applies to water ($H_2O$), it can also apply to other liquids that are desirably removed from a sample in a drying process.

In this regard, it is similarly well understood by those familiar with the chemical arts that when changes of state or chemical reactions require heat to proceed, that there are periods during the reaction at which all of the heat will be absorbed into the change of state (heat of fusion, heat of vaporization) or into the chemical reaction (heat of reaction; $\Delta H$), and will not produce a change of temperature. Once the change of state or chemical reaction is complete, however, any energy applied will tend to thermally raise the temperature of the products. This immediate change in temperature can be monitored and, using the microwave techniques of the present invention, microwave energy can be immediately moderated in response as desired or necessary. In contrast, oven, flame, or hot plate heating are more drawn out processes, and the addition or cessation of heat can be neither accurately monitored nor quickly controlled.

Accordingly, in another embodiment, the invention can comprise the method of rapidly monitoring and controlling a chemical process by monitoring the temperature of a chemical composition (including compositions undergoing chemical and physical reactions), while applying microwave radiation to the composition. Any rapid change in the temperature of the composition that indicates a change of state or completion of a chemical reaction is thus identified, and the application of microwave radiation to the composition is immediately moderated. As in all of the other embodiments, the moderation of the microwave radiation can comprise moderating the passage of microwaves from the microwave source to the composition without moderating the production of microwaves by the source, and the monitoring of the temperature preferably comprises the use of an infrared pyrometer. Furthermore, the step of monitoring the temperature, in this and the other embodiments, can comprise measuring the temperature of the composition, or can comprise measuring the temperature of the reaction vessel containing the composition. In either case, once an appropriate accurate temperature is measured, the reaction can be appropriately controlled by moderating the application of microwave radiation.

The method of the invention is particularly suited for reactions such as analytical digestion. Although the term "digestion" is used to refer to a variety of chemical and biological processes, in one sense it refers to the oxidation and reduction of materials into their basic elements to thereby identify those elements, and thus characterize the material that has been digested. As is sometimes useful in digestion analysis, the method can further comprise one or more steps of ramping the temperature of the first reagent, both reagents, or the solvent system, either prior to the step of adding other reagents, or following the step of adding the respective reagents. As used herein, the term "ramping" means controlling the temperature of a system as the system is heated or cooled, and can include defining the rate of heating or cooling, as well as providing periods of constant temperature between various heating and cooling steps.

In a common useful embodiment of the invention, the step of adding a portion of the second reagent to a heated portion of the first reagent will often comprise adding nitric acid ($HNO_3$) to sulfuric acid ($H_2SO_4$) in the presence of some other material that is to be digested and thus analyzed.

The method aspects of the invention offer a number of advantages, particularly in conjunction with the apparatus disclosed in the copending incorporated application. For example, the ability to control temperature based on feedback temperature measurements can be used to hold the temperature of the contents of a reaction vessel above the boiling point of the incrementally added reagent or reagents during addition, after addition, or both, so that the reaction can be carried out at elevated temperatures and thus proceed more rapidly.

As is well known to those familiar with the basic principles of chemical reactions and reaction rates ("kinetics"), many reactions proceed much more rapidly at elevated temperatures, some geometrically faster and some exponentially faster.

Furthermore, because the invention provides a method of carrying out high temperature reactions at atmospheric pressure, it eliminates the inherent dangers present when a pressurized system is used to elevate reagents above their normal boiling points.

Additionally, because the invention provides the apparatus and method for carrying out high temperature reactions at atmospheric pressure, the gaseous by-products generated by typical reactions (such as acid digestion) do not build up pressure in dangerous fashion, but instead can be vented in a normal fashion to the atmosphere which, for purposes of laboratory chemical reactions, has an infinite gas volume capacity.

The invention also eliminates the necessity of catalysts to increase the rate of reactions at atmospheric pressure, although catalysts can certainly be used in conjunction with the invention if desired for some other purpose.

By eliminating the need for a high pressure apparatus to run reactions at temperatures above the normal boiling points of the solvents or the reagents, the invention likewise eliminates the associated steps otherwise required for carrying out a continuous reaction at high temperature and high pressure: i.e., reducing the pressure to room temperature, adding additional reagent, re-elevating the pressure, re-raising the temperature and thus resuming the reaction.

For example, in some conventional microwave digestion techniques, temperatures of about 200° C. can be generated at pressures of up to about 220 pounds per square inch (psi) in closed vessels using nitric acid (boiling point at atmospheric pressure of 120.5° C.). Using the invention, the same digestion reaction can be performed at temperatures equivalent to closed vessel systems (i.e., about 200° C.) but utilizing relatively small amounts (e.g., 1 to 10 milliliters) of sulfuric acid at atmospheric pressure (atmospheric pressure boiling point of 330° C.) as the high temperature environment. The addition of suitable oxidizing reagents such as nitric acid, other acids, or even hydrogen peroxide ($H_2O_2$) can then be carried out at temperatures above 200° C. at atmospheric pressure and using microwave feedback control.

It will be understood, of course, that the invention is not limited to atmospheric pressure but that it provides the opportunity to operate at atmospheric pressure as may be desired or necessary.

FIG. 1 is an artist's rendering of one version of such a device broadly designated at 10. The device 10 includes a housing 11, a plurality of reaction cells 12 to hold respective reaction vessels 13 (usually formed of glass) with a cold trap, vent, or reflux apparatus 14 associated therewith. The device 10 illustrated in FIG. 1 also includes a vapor containment system broadly designated at 15, a reagent addition system illustrated as the fixture 16 that cooperate with the glass vessels 13, and individual controls 18 for each of the reaction cells 12.

Figure 2:
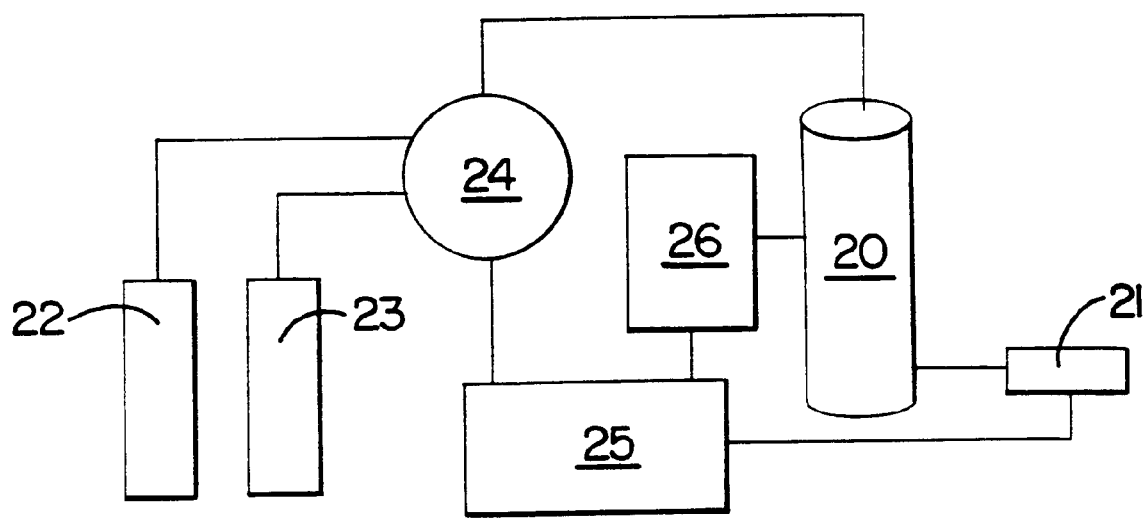
FIG. 2 is a schematic diagram that illustrates the method of the invention.

FIG. 2 is a schematic diagram (and not to scale) that illustrates the method of the invention. In FIG. 2, a reaction vessel is designated at 20, an infrared pyrometer at 21, reagent sources at 22 and 23, a pump at 24, a microprocess at 25, and a source of microwave radiation 26. As previously described herein, the pyrometer 21 monitors the temperature of the reaction vessel 20, and sends the information to the microprocessor 25. Based upon the temperature, the microprocessor 25 controls the pump 24 and the microwave source 26 to either add reagent from the sources 22 and 23, moderate the microwave energy from its source 26, or both, to control a reaction in a desired manner.

EXAMPLES

The following examples are representative of some processes that can be carried out according to the present invention, and for which the apparatus described in the concurrently filed application noted above ("Microwave Apparatus for Controlling Power Levels in Individual Multiple Cells") is particularly suitable.

The times for the methods can be calculated by adding the times for the stages. Reagents can be added in three separate instances; initially—right at the start of the method, on the ramp—right at the start of the stage and over the TAP (Time at Parameter). When selecting a reagent addition the user is prompted to input values for the total volume of reagent added during that stage as well as an aliquot size for this volume. Hence if 10 milliliters (mL) of nitric acid are to be added over a 5 minute TAP in aliquots of 1 mL the unit will automatically spread the additions out evenly over the TAP. In the above circumstance a 1 mL addition will be made every 30 seconds for the 5 minute duration of the TAP totalling 10 mL. During this period the temperature is feedback controlled to maintain the desired setpoint and avoid any thermal dilution which can be severely dependent upon the relative volumes of the liquid in the sample vessel and the liquid being added. If, however, additions are made initially or on the ramp, the total volume of reagent is added in the selected aliquot size with no regard to any selected times. The additions under these circumstances are simply made before the start of the method or stage as applicable.

EXAMPLE 1

Digestion of 1 g sample of plant material (e.g. pine needles) for elemental analysis.

| STAGE | RAMP TIME | TEMP | TAP TIME | REAGENT |
|---|---|---|---|---|
| 1 | 3 mins | 130° C. | 0 | 12 ml nitric/2.5 ml sulfuric added initially |
| 2 | 2 mins | 200° C. | 1 min | 2 ml nitric added on TAP/1 ml aliquots |
| 3 | 2 mins | 250° C. | 5 mins | 10 ml nitric added on TAP/ml aliquots |
| 4 | 0 (cools down) | 200° C. | 10 mins | 20 ml hydrogen peroxide on TAP/1 ml aliquots |

EXAMPLE 2

Digestion of 1 g of Epoxy Glue for elemental analysis.

| STAGE | RAMP TIME | TEMP | TAP TIME | REAGENT |
|---|---|---|---|---|
| 1 | 2 mins | 125° C. | 5 mins | 15 ml nitric/3 ml sulfuric added initially |
| 2 | 1 mins | 200° C. | 0 | |
| 3 | 1 min | 270° C. | 5 mins | 2 ml nitric added on ramp |
| 4 | 0 | 200° C. | 2.5 mins | 10 ml peroxide added on TAP/1 ml aliquots |
| 5 | 1 min | 270° C. | 0 | 2 ml nitric added on ramp |
| 6 | 0 | 200° C. | 2.5 mins | 10 ml peroxide added on TAP/1 ml aliquots |

EXAMPLE 3

Digestion of 2 g of polypropylene for elemental analysis.

| STAGE | RAMP TIME | TEMP | TAP TIME | REAGENT |
|---|---|---|---|---|
| 1 | 3 mins | 90° C. | 0 | 20 mL sulfuric initially |
| 2 | 5 mins | 150° C. | 10 secs | 2 ml nitric on TAP/1 mL aliquots |
| 3 | 5 min | 210° C. | 0 | |
| 4 | 5 mins | 270° C. | 0 | |
| 5 | 0 | 250° C. | 10 mins | 20 ml nitric added on TAP/1 mL aliquots |
| 6 | 0 | 200° C. | 10 mins | 20 ml peroxide added on TAP/1 ml aliquots |

EXAMPLE 4

Catalyst free Kjeldahl digest for elemental nitrogen analysis. Sample—1 g of pine needles.

It will be understood that the object of Kjeldahl digests is to first char or carbonize the sample with sulfuric acid at high temperatures, then oxidize the organic components to free up the nitrogen and convert it to ammonium compounds which are reduced to ammonia and detected during the analysis. Obviously nitric acid cannot be used. Conventionally these digests are very time consuming and take hours. Catalysts such as mercury oxides are used to assist the digestion/reduction

| STAGE | RAMP TIME | TEMP | TAP TIME | REAGENT |
|---|---|---|---|---|
| 1 | 3 mins | 200° C. | 0 | 20 mL sulfuric initially |
| 2 | 1 mins | 250° C. | 0 | |
| 3 | 1 min | 300° C. | 0 | |
| 5 | 0 | 250° C. | 5 mins | 10 ml peroxide added on TAP/1 ml aliquots |

EXAMPLE 5

Catalyst free Kjeldahl digestion of 1 g of nicotinic acid.

In this instance it will be understood that nicotinic acid contains nitrogen incorporated into a very tightly bound structure. Nicotinic acid is generally well recognized as the single most difficult Kjeldahl digest.

| STAGE | RAMP TIME | TEMP | TAP TIME | REAGENT |
|---|---|---|---|---|
| 1 | 3 mins | 200° C. | 0 | 20 mL sulfuric initially |
| 2 | 1 mins | 250° C. | 0 | |
| 3 | 1 min | 300° C. | 0 | |
| 4 | 1 mins | 350° C. | 0 | |
| 5 | 0 | 200° C. | 8 mins | 32 ml peroxide added TAP/2 mL aliquots |
| 6 | 1 | 350° C. | 0 | |
| 7 | 0 | 200° C. | 7 mins | 28 ml peroxide added on TAP/2 ml aliquots |

The above method had 6 g of potassium sulphate added to the sample as a solid before the method was run. This was to increase the boiling point of the sample/reagent mixture and allow a temperature of at least 350° C. to be achieved.

In the specification, there have been disclosed typical preferred embodiments of the invention and, although specific terms have been employed, they have been used in a generic and descriptive sense only and not for purposes of limitation, the scope of the invention being set forth in the following claims.

That which is claimed is:

1. A method of increasing the rate of chemical reactions while controlling an elevated temperature for the reactions, the method comprising:

adding a portion of a second reagent to a heated and proportionally larger portion of a first reagent at atmospheric pressure, with at least one of said reagents being thermally responsive to electromagnetic radiation in the microwave range;

maintaining the reagents at atmospheric pressure: while monitoring the temperature of the admixture of said first and second reagents as the second reagent is added; and applying sufficient microwave radiation from a microwave source to the admixture of said first and second reagents based on the monitored temperature to continuously maintain the added reagents at or closely about the predetermined temperature while substantially avoiding thermal dilution that would otherwise be caused by the addition of the reagents to an one another.

2. A method according to claim 1 wherein the steps of adding the reagents, monitoring their temperature and applying microwave radiation are all carried out with the reagents at atmospheric pressure.

3. A method according to claim 1 wherein the steps of adding the second reagent to the first reagent comprises adding the second reagent to a proportionally larger portion of the first reagent.

4. A method according to claim 1 wherein the step of adding the second reagent to the first reagent comprises adding a liquid to a liquid.

5. A method according to claim 4 wherein the step of adding the second liquid to the first liquid comprises adding the second liquid while the heated first liquid is being maintained at atmospheric pressure and at a predetermined temperature that is above the boiling point of the second reagent.

6. A method according to claim 4 wherein the step of applying microwave radiation comprises applying microwave radiation while maintaining the added first and second liquids at atmospheric pressure and at the predetermined temperature.

7. A method according to claim 1 and further comprising the step of ramping the temperature of the first reagent prior to the step of adding the second reagent.

8. A method according to claim 1 and further comprising the step of ramping the temperature of the first reagent following the step of adding the second reagent.

9. A method according to claim 1 wherein the step of adding the second reagent to the first reagent comprises adding a liquid to a solid.

10. A method according to claim 1 wherein the step of adding the second reagent to the first reagent comprises adding a solid to a liquid.

11. A method according to claim 1 wherein the step of adding the second reagent to the first reagent comprises adding a solid to a solid.

12. A method according to claim 1 wherein the step of adding the second reagent to the first reagent comprises incrementally adding the second reagent to the first reagent.

13. A method according to claim 1 and further comprising the step of heating the first reagent prior to the step of adding the second reagent.

14. A method according to claim 1 wherein the step of applying microwave radiation comprises applying the microwave radiation on a time-continuous basis while moderating the amount of the continuously applied energy that is applied to the added first and second reagents.

15. A method according to claim 1 wherein that step of monitoring the temperature comprises monitoring the infrared radiation emitted from the reagents.

16. A method according to claim 1 wherein the step of applying microwave radiation comprises applying sufficient microwave radiation to heat the sample to and keep the sample at a predetermined temperature.

17. A method according to claim 1 wherein the step of applying microwave radiation comprises applying sufficient microwave radiation to heat the sample to and keep the sample within a predetermined temperature range.

18. A method according to claim 1 wherein the step of adding respective portions of a first reagent and a second reagent further comprises adding the reagents at atmospheric pressure to a heated and proportionally larger portion or a solvent system that has dielectric properties responsive to microwave radiation, and with said solvent system also at atmospheric pressure and at a predetermined temperature.

19. A method according to claim 18 wherein the step of adding the reagents to the heated solvent system comprises adding the reagents to a solvent system that is heated to a predetermined temperature above the boiling point of at least one of the first or second reagents.

20. A method of increasing the rate of chemical reactions while controlling an elevated temperature for the reactions, the method comprising;

adding an incremental portion of a second reagent to a heated and proportionally larger portion of a first reagent, with at least one of said reagents being thermally responsive to electromagnetic radiation in the microwave range;

maintaining the reagents at atmospheric pressure, while monitoring the temperature of the admixture of said first and second reagents as the second reagent is added;

applying sufficient microwave radiation to the admixture of said first and second reagents to substantially avoiding thermal dilution that would otherwise be caused by the addition of the reagents to one another, and identifying the exhaustion of the incrementally added second reagent based upon change in the monitored temperature of the added first and second reagents; and thereafter adding another incremental portion of said second reagent to the heated and proportionally larger portion of the first reagent.

21. A method according to claim 20 and further comprising the step of heating the first reagent prior to the step of adding the second reagent.

22. A method according to claim 20 wherein the step of adding another incremental portion of reagent comprises adding another incremental portion of the second reagent.

23. A method according to claim 20 wherein the step of adding another incremental portion or reagent comprises adding another incremental portion of a reagent other than the second reagent.

24. A method of increasing the rate of chemical reactions while controlling an elevated temperature for the reactions, the method comprising:

applying sufficient microwave radiation in the temperature monitored mixture of two reagents at atmospheric pressure, with at least one of said reagents being thermally responsive to electromagnetic radiation in the microwave range, and based on the monitored temperature, to continuously maintain the added reagents at or closely about a predetermined temperature while substantially avoiding thermal dilution that otherwise would have been caused by the addition of the reagents to one another.

25. A method according to claim 24 and further comprising the step of forming the mixture by adding a portion of the second reagent to a heated and proportionally larger portion of the first reagent.

26. A method according to claim 24 wherein the step of applying the microwave radiation further comprises moderating the passage of microwaves from the microwave source to the composition without moderating the production of microwaves by the source.

27. A method of rapidly monitoring and controlling a chemical process, the method comprising:

monitoring the temperature of a chemical composition at atmospheric pressure while applying microwave radiation to the composition;

identifying a rapid change in the temperature of the composition that indicates a change of state or completion of a chemical reaction; and immediately moderating the microwave radiation applied to the composition.

28. A method according to claim 27 wherein the step of monitoring the temperature comprises monitoring the temperature with an infrared pyrometer.

29. A method according to claim 28 wherein the step of monitoring the temperature comprises measuring the temperature of the composition.

30. A method according to claim 28 wherein the step of monitoring the temperature comprises measuring the temperature of the reaction vessel containing the composition.

31. A method according to claim 28 wherein the step of immediately moderating the microwave radiation comprises preventing microwave radiation from reaching the sample.

32. A method of increasing the rate of chemical reactions at atmospheric pressure, while controlling an elevated temperature for the reactions, the method comprising:

adding a portion of a second reagent at atmospheric pressure to a heated and proportionally larger portion of a first reagent also at atmospheric pressure, while the heated first reagent is being maintained at atmospheric pressure and at a predetermined temperature that is above the boiling point of the second reagent, and while monitoring the temperature of the admixture of said first and second reagents, and while continuously maintaining the admixture of said first and second reagents at atmospheric pressure and at the predetermined temperature.

33. A method according to claim 32 and further comprising the step of heating the first reagent prior to the step of adding the second reagent.

34. A method according to claim 32 wherein the step of maintaining the added first and second reagents at the predetermined temperature comprises applying electromagnetic radiation in the microwave range to the reagents.

35. A method according to claim 34 wherein the step of applying the microwave radiation further comprises moderating the passage of microwaves from the microwave source to the composition without moderating the production of microwaves by the source.

36. A method according to claim 34 wherein the step of applying electromagnetic radiation in the microwave range comprises adding microwave radiation based upon the monitored temperature of the added first and second reagents.

37. A method according to claim 32 wherein the step of adding a portion of the second reagent comprises adding an incremental portion of the second reagent.

38. A method according to claim 32 and further comprising the step of ramping the temperature of the first reagent prior to the step of adding the second reagent.

39. A method according to claim 32 and further comprising the step of ramping the temperature of the first reagent following the step of adding the second reagent.

40. A method according to claim 32 wherein the step of adding a portion of the second reagent to a heated portion of the first reagent comprises adding nitric acid to sulfuric acid.

* * * * *